(12) United States Patent
Manhes

(10) Patent No.: US 7,131,985 B1
(45) Date of Patent: *Nov. 7, 2006

(54) TROCAR SLEEVE FOR ENDOSCOPIC APPLICATIONS

(75) Inventor: Hubert Manhes, Vichy (FR)

(73) Assignee: Karl Storz GmbH & Co. (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 894 days.

(21) Appl. No.: 09/214,875

(22) PCT Filed: Jul. 22, 1997

(86) PCT No.: PCT/DE97/01552

§ 371 (c)(1),
(2), (4) Date: Apr. 19, 1999

(87) PCT Pub. No.: WO98/03121

PCT Pub. Date: Jan. 29, 1998

(30) Foreign Application Priority Data

Jul. 28, 1996 (DE) .............................. 196 29 537

(51) Int. Cl.
*A61B 17/34* (2006.01)

(52) U.S. Cl. .................... 606/185; 606/104; 604/161
(58) Field of Classification Search .................... 606/1, 606/104–108, 181–185; 604/104–109, 164, 604/280, 174, 175, 178, 161; 600/566, 567, 600/564; 30/173, 175, 187

See application file for complete search history.

(56) References Cited

U.S. PATENT DOCUMENTS

| | | | |
|---|---|---|---|
| 3,877,429 A * | 4/1975 | Raumoff ...................... 604/158 |
| 5,263,937 A | 11/1993 | Shipp | |
| 5,279,564 A | 1/1994 | Taylor | |
| 5,279,575 A * | 1/1994 | Sugarbaker | |
| 5,320,627 A * | 6/1994 | Sorensen et al. ............ 606/127 |
| 5,354,302 A * | 10/1994 | Ko .............................. 606/104 |
| 5,595,186 A * | 1/1997 | Rubinstein et al. .......... 600/564 |
| 5,620,456 A * | 4/1997 | Sauer et al. ................. 606/185 |
| 5,885,226 A * | 3/1999 | Rubinstein et al. .......... 600/564 |
| 6,030,364 A * | 2/2000 | Durgin et al. .......... 604/164.01 |

FOREIGN PATENT DOCUMENTS

| | | |
|---|---|---|
| DE | 82 16 373.1 | 9/1982 |
| DE | 42 38 596 A1 | 6/1994 |
| DE | 43 07 228 A1 | 9/1994 |
| EP | 0 577 400 A1 | 1/1994 |
| EP | 0 614 646 A1 | 9/1994 |

* cited by examiner

*Primary Examiner*—Vy Q. Bui
(74) *Attorney, Agent, or Firm*—St. Onge Steward Johnston & Reens LLC

(57) ABSTRACT

What is described here is a trocar sleeve for endoscopic applications, comprising an elongate part including at least one passage for insertion of an instrument such as an endoscopic, scissors or the like, and pivotable parts mobile on the distal end. The inventive trocar sleeve is characterized by the provision that the distal section is formed by several longitudinal sections articulated on the proximal section of the trocar sleeve, and that a mechanism is provided for pivoting the individual longitudinal sections about an axis orthogonal on the longitudinal axis of the trocar sleeve.

8 Claims, 2 Drawing Sheets

TROCAR SLEEVE FOR ENDOSCOPIC APPLICATIONS

This application is a 371 of PCT/DE 97/01552 filed Jul. 22, 1997 under the International Convention and based on a German Application DE19629537.8-35 filed Jul. 22, 1996.

1. Field of the Invention

The present invention relates to a trocar sleeve for endoscopic applications in surgical and diagnostic procedures involving use of an endoscope scissors and the like.

2. Prior Art

Typical trocar sleeves comprise a cylindrical section with at least one passage for insertion of an instrument such as a trocar mandrel, an endoscope, scissors or the like. The majority of the trocar sleeves presently available in the market has a length which exceeds the thickness of the wall of the body cavity substantially, such as the abdominal wall through which the trocar or the trocar sleeve is introduced into the interior of the body. One of the reasons is the fact that a trocar which is too short can neither be well seized nor guided in introduction in practice. Thus the cylindrical tubular section of the trocar sleeve restricts that part of the body cavity which is accessible with a flexible instrument or with an instrument having a diameter smaller than the trocar passage diameter.

This disadvantage exists also in the trocar sleeve known from the German Patent DE 43 07 228 A1—from which the wording of the introductory clause of Patent claim 1 starts out:

This trocar sleeve consists of two sleeves whereof the outer one is provided with mobile pivotable parts such as segments, platelets, rods, etc. The inner sleeve, by contrast, has a rigid configuration of the kind of known trocars.

Corresponding statements apply also to the trocar sleeve known from the German utility model DE 81 16 373 U1 which comprises terminal sections that may be spread apart but not pivoted.

BRIEF DESCRIPTION OF THE INVENTION

The present invention is based on the problem of providing a trocar sleeve which, during the operation of introduction into a body cavity, presents a length so long that it is suitable for handling it in an ergonomic and safe way while, upon introduction into the body cavity, it does yet not obstruct the operation in the body cavity by projecting too far into the body cavity.

Another problem underlying the invention is the provision of a trocar sleeve which can be introduced into a body cavity, e.g. by penetration of the abdominal wall, without the need to use a trocar mandrel.

Inventive solutions to the problem are supported by the common basic idea that longitudinal portions pivotable about an axis orthogonal on the longitudinal axis of the trocar sleeve form the distal section of the trocar sleeve. When after introduction of the trocar sleeve into the body cavity the longitudinal sections are pivoted outward the effective length of the trocar sleeve is reduced. Hence a flexible or bendable instrument can reach a larger part of the body cavity than would be possible with a conventional trocar sleeve which projects into the body cavity over a comparatively long distance. The maneuverability of the trocar sleeve is yet unrestricted when the body wall, e.g. the abdominal wall, is pierced through because the trocar or the trocar sleeve, respectively, has a length permitting convenient seizing.

As has been set out above an apparatus in accordance with the invention provides a trocar sleeve which is split in its distal terminal section in the longitudinal direction so that it consists of several longitudinal sections. The individual longitudinal sections can be tilted outward in a direction towards the proximal end upon introduction of the trocar sleeves. Hence the opening cone, which is released by the passage(s) of the trocar sleeve for flexible or bendable instruments, respectively, can be substantially widened, compared against conventional trocar sleeves. Even if instruments with a diameter definitely smaller than the diameter of the passage are passed through the passage in an "oblique" position a substantially larger space can be "operated on".

The outwardly pivotable longitudinal sections can be used not only for an enlargement of the space accessible to instruments in the body cavity but also for fastening or fixing the trocar sleeve at the wall of the body cavity, e.g. the abdominal wall.

To this end the longitudinal sections are adapted for bearing against the internal wall of the body cavity into which the trocar sleeve is inserted. It is a particular advantage when the longitudinal sections are configured in the way of wings because in such a case the longitudinal sections adhere against a large area on the body wall.

The basic inventive idea of splitting the distal section of the trocar sleeve in the longitudinal direction and to configure the individual longitudinal sections for pivoting is useful not only for enlarging the achievable "opening cone" but also for configuring the longitudinal sections for forward tilting in such a way that they form a tip (claim 9). It might be necessary to provide the individual sections with a blade or a tip, respectively, so that also the conically forward-tilted longitudinal sections have a common tip as well. In this way it is possible to dispense with the pointed trocar mandrel and to "push" the trocar sleeve through the body wall directly without an additional mandrel on account of the trocar tip.

In another embodiment a flange is provided on the proximal end of the trocar sleeve, by which the trocar sleeve bears against the outer wall of the body cavity. The trocar sleeve can hence be fastened on the body wall in the manner of "tongs handles" whilst it is supported from inside by the wings or the outwards tilted longitudinal sections.

It is preferred to have a handle adjustable in the longitudinal direction because in such a case the body wall can be "clamped" between the flange and the swing-out longitudinal sections.

The mechanism which serves to tilt the longitudinal sections inward and/or outward can be realised in the most different ways:

It is possible, for instance, to provide transmission elements such as wire controls, rods, etc. for managing the tilting manoeuvre. A particularly simple solution consists of the mechanism includes spring elements which bias the individual longitudinal sections in a direction towards the proximal end. In their "inoperative position" or resting position the longitudinal sections are tilted inward so as to form the tip. Upon piercing through the body wall an instrument such as an endoscope is introduced. By this action the longitudinal sections are forcibly pivoted outward. As soon as the position of the longitudinal sections exceeds a certain angle the spring action causes the longitudinal sections to rotate outward so that they can bear against the inside of the body cavity, e.g. the inside of the abdominal wall, in particular.

For withdrawal of the trocar sleeve from the body cavity the bearing support of the longitudinal sections against the inside of the body cavity causes the sections to pivot forward so that the trocar sleeve can be removed without any problems. The instrument may remain in the passage of the trocar sleeve during this operation.

The inventive trocar can practically employed in all fields of endoscopy, e.g. in coelioscopy or laparoscopy and even in engineering applications.

BRIEF DESCRIPTION OF THE DRAWING

The following is an exemplary description of the invention without any restriction of general inventive idea, with reference to the drawing which is explicitly references in all other respects as far as the disclosure of all inventive details is concerned which are not explained in more details in the text. In the drawing.

DESCRIPTION OF AN EMBODIMENT

Figure 1:
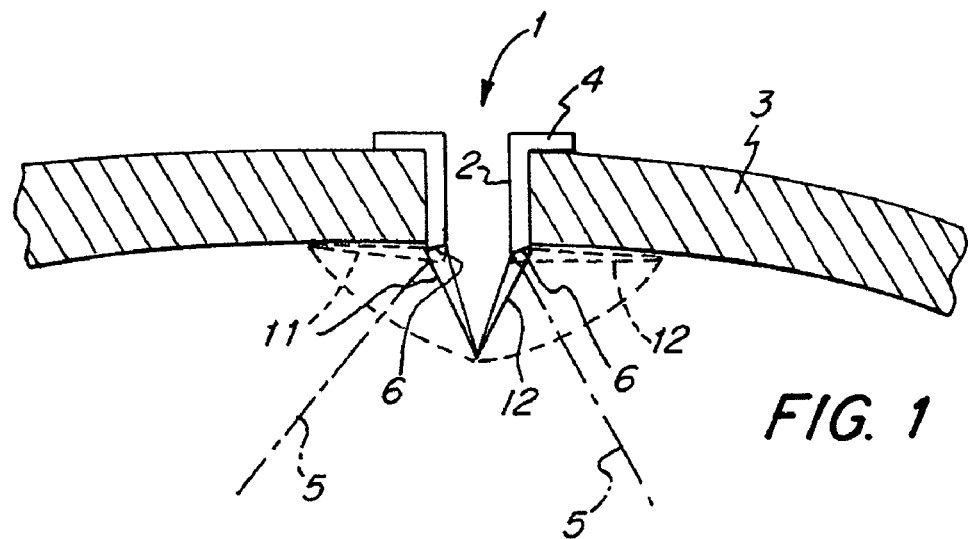
FIG. 1 is a longitudinal sectional view taken through an inventive trocar sleeve.

FIG. 1 shows an inventive trocar sleeve 1. The trocar sleeve is split in the longitudinal direction in its distal terminal section so that it consists of several—in the illustrated embodiment—four—longitudinal sections of which FIG. 1 represents only the longitudinal portions 11 and 12. However, also two, three or more, e.g. five, longitudinal sections are conceivable and possible.

The longitudinal portions 11, 12 . . . are articulated at a cylindrical central portion 2 of the trocar sleeve 1 by means of joints 6 for pivoting whilst they can be pivoted via appropriate actuating elements from the proximal end or by means of a spring action.

It is possible, for instance, that spring elements in the joints 6 act upon the individual longitudinal portions 11, 12, . . . to bias them in a direction toward the proximal end. The longitudinal sections are normally tilted inward so as to form the tip illustrated by the continuous lines. Each of the sections is provided with a blade 10, that may be made integrally with the blade, so that longitudinal sections have a common tip as well. During insertion of the trocar 1 it is hence possible to dispense with a trocar mandrel for cutting through the body cavity such as the abdominal wall 3.

Upon insertion of the trocar sleeve 1 the individual longitudinal portions (11, 12) are tilted outward until they bear against the internal wall of the abdominal wall 3. This is illustrated in FIG. 1 by dashed lines. The pivoting movement is symbolically indicated by dashed lines.

In the event of application of spring-biased joints 6 it is possible, for instance to insert an instrument such as an endoscope upon piercing of the body wall. As a result, the longitudinal sections are forcibly tilted outward. As soon as the position of the longitudinal sections exceeds a certain angle the spring action causes the longitudinal sections to tilt outward and to bear against the inside of the body cavity.

Figure 3:
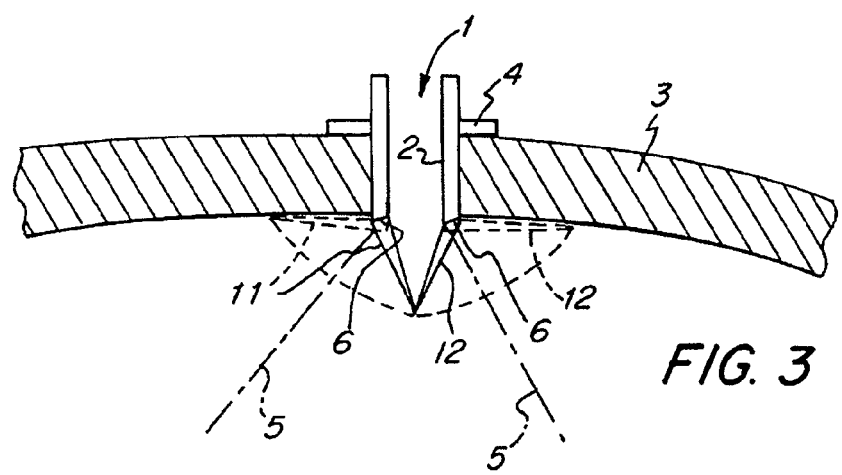
FIG. 3 shows an embodiment of the trocar sleeve of FIG. 1.

A flange 4 is provided on the proximal end of the trocar sleeve 1, by which the trocar sleeve 1 bears against the outer wall of the abdominal wall for fixing the trocar by "clamping" the abdominal wall between the flange 4 and the longitudinal portions 11, 12. To this end the flange 4 may be adjustable in the longitudinal direction along the central portion 2, as shown in FIG. 3.

For withdrawal of the trocar sleeve from the body cavity the longitudinal portions 11, 12, . . . , on account of their bearing against the inside of the abdominal wall 3, are caused to pivot forward so that the trocar sleeve may be withdrawn without any problems.

The chain-dot lines illustrate the space 5 which is accessible for an instrument—which is not shown here.

Figure 2:
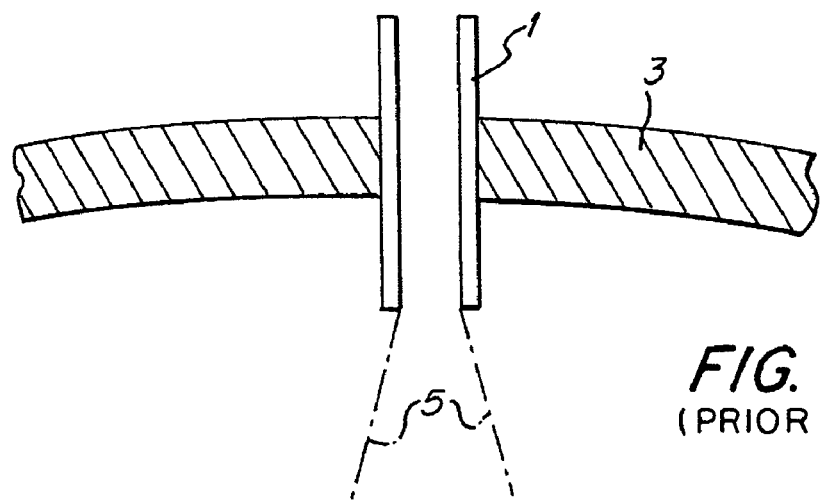
FIG. 2 shows a conventional trocar sleeve.

For comparison, FIG. 2 shows the space 5 which is accessible with a conventional trocar 1—which merely consists of a long tubular section 2'. As is apparent from a comparison of the Figures, the inventive trocar renders a substantially wider space accessible. Moreover, a separate trocar mandrel can be dispensed with.

It is possible, for instance, to control the longitudinal portions 11, 12, . . . by cable controls, lever joints or by an operating mechanism suitable for insertion into the trocar passage, rather than by spring-biased joints 6.

The invention claimed is:

1. Trocar sleeve for endoscopic applications, comprising:
   an elongate part having at least one passage for insertion of a surgical instrument, and
   pivotable parts formed at a distal section of the elongate part, each having a blade end portion, the pivotable parts converging toward one another in a piercing position, wherein the blade end portions of the pivotable parts form a pointed tip which permits the cutting of a body wall without an additional trocar mandrel.

2. The trocar sleeve defined in claim 1 wherein the distal section of the elongate part has a plurality of spring elements between the elongate part and the pivotable parts for biasing the pivotable parts toward the piercing position.

3. The trocar sleeve defined in claim 2 wherein the spring-biased joints bias the pivotable parts away from one another to an operative position upon displacement of the surgical instrument along one passage after cutting the body wall.

4. The trocar sleeve defined in claim 3 wherein the pivotable parts bear against an inner side of the body wall in the operative position.

5. The trocar sleeve defined in claim 1 wherein each of the pivotable parts is configured as a wing.

6. The trocar sleeve defined in claim 2 wherein each of the spring-biased joints acts upon a respective individual pivotable part.

7. Trocar sleeve for endoscopic applications, comprising:
   an elongate part having at least one passage for insertion of a surgical instrument, and
   pivotable parts formed at a distal section of the elongate part, each having a blade end portion, the pivotable parts converging toward one another in a piercing position, wherein the blade end portions of the pivotable parts form a pointed tip which permits the cutting of a body wall without an additional trocar mandrel and wherein the distal section has a flange bearing against an outer side of the body wall.

8. The trocar sleeve defined in claim 7 wherein the flange is displaceable along the distal section of the elongate part.

* * * * *